US009442124B2

(12) United States Patent
Cornelli

(10) Patent No.: US 9,442,124 B2
(45) Date of Patent: Sep. 13, 2016

(54) METHOD FOR DETERMINING THE ANTIOXIDANT POWER OF BIOLOGICAL OR VEGETAL FLUIDS

(75) Inventor: Umberto Cornelli, Milan (IT)

(73) Assignee: COR.CON INTERNATIONAL, S.R.L. (IT)

( * ) Notice: Subject to any disclaimer, the term of this patent is extended or adjusted under 35 U.S.C. 154(b) by 1051 days.

(21) Appl. No.: 13/579,545

(22) PCT Filed: Feb. 23, 2011

(86) PCT No.: PCT/EP2011/052669

§ 371 (c)(1),
(2), (4) Date: Aug. 16, 2012

(87) PCT Pub. No.: WO2011/104267

PCT Pub. Date: Sep. 1, 2011

(65) Prior Publication Data

US 2012/0309102 A1 Dec. 6, 2012

(30) Foreign Application Priority Data

Feb. 25, 2010 (EP) .................................... 10425050

(51) Int. Cl.
*G01N 33/84* (2006.01)
*G01N 33/82* (2006.01)

(52) U.S. Cl.
CPC .............. *G01N 33/84* (2013.01); *G01N 33/82* (2013.01)

(58) Field of Classification Search
None
See application file for complete search history.

(56) References Cited

U.S. PATENT DOCUMENTS 3,382,924 A 5/1968 Veley et al.
5,019,149 A * 5/1991 Hawkins et al. ................. 71/29
6,177,260 B1 * 1/2001 Benzie ................... G01N 33/82 435/25

FOREIGN PATENT DOCUMENTS

WO 9725463 A1 7/1997

OTHER PUBLICATIONS

Edson "The Comber soil acidity test for soluble iron in Azalea soils," Proceedings of the Florida State Horticultural Society, 1959, 72, 380-383.*

Moon, J.-K. et al. "Antioxidant Assays for Plant and Food Components," J. Agric. Food Chem. 2009, 57, 1655-1666.*

Palmieri, B. et al. "Oxidative stress tests: overview on reliability and use: Part II" European Review for Medical and Pharmacological Sciences, 2007; 11: 383-399.*

Hu, M.Z.C., et al., "Sol-Gel and Ultrafine Particle Formation via Dielectric Tuning of Inorganic Salt-Alcohol-Water Solutions", Journal of Colloid and Interface Science, vol. 222, pp. 20-36, 2000.

Moon, Y.T, et al., "Preparation of Monodisperse and Spherical Zirconia Powders by Heating of Alcohol-Aqueous Salt Solutions", Journal of the American Ceramic Society, vol. 78, No. 10, pp. 2690-2694, 1995.

Neagu, R., et al., "Initial Stages in Zirconia Coatings Using ESD", Chemistry of Materials, vol. 17, pp. 902-910, 2005.

Shanmugasundaram, P., et al., "Hepatoprotective and antioxidant effects of Hygrophila auriculata (K. Schum) Heine Acanthaceae root extract", Journal of Ethnopharmacology, vol. 104, pp. 124-128, 2006.

Wu, Z.G. et al., "Preparation and characterization of Zr02 aerogel", Journal of Functional Materials, vol. 35, No. 3, pp. 389-391, Jun. 2004, (abstract only).

Battino, M. et al., "The antioxidant capacity of saliva", Journal of Clinical Periodontology, 2002, vol. 29, pp. 189-194, Denmark.

Benzie, I.F.F. et al., "Ferric Reducing/Antioxidant Power Assay: Direct Measure of Total Antioxidant Activity of Biological Fluids and Modified Version for Simultaneous Measurement of Total Antioxidant Power and Ascorbic Acid Concentration", Methods in Enzymology, 1999, vol. 299, pp. 15-27.

Benzie, I.F.F. et al., "The Ferric Reducing Ability of Plasma (FRAP) as a Measure of "Antioxidant Power": The FRAP Assay", Analytical Biochemistry, 1996, vol. 239, pp. 70-76.

Borges Jr., I. et al., "Prinflammatory and Oxidative Stress Markers in Patients with Periodontal Disease", Mediators of Inflammation, 2007, vol. 2007, pp. 1-5.

Celi, P. et al., "The stability of the reactive oxygen metabolites (d-ROMs) and biological antioxidant potential (BAP) tests on store horse blood", The Veterinary Journal, 2010, vol. 183, pp. 217-218.

Del Vigna De Almeida, P. et al., "Saliva Composition and Functions: A Comprehensive Review", The Journal of Contemporary Dental Practice, 2008, vol. 9, No. 3, pp. 1-11.

Dick, W.A. et al., "Determinatino of Orthophosphate in Aqueous Solutions Containing Labile Organic and Inroganic Phosphorous Compounds", Journal of Environmental Quality, 1977, vol. 6, No. 1, pp. 82-85.

Grisham, M.B. et al., "Cytotoxic properties of salivary oxidants", The American Physiological Society, 1990, pp. C115-C121.

(Continued)

*Primary Examiner* — Yelena G Gakh
*Assistant Examiner* — Michelle Adams
(74) *Attorney, Agent, or Firm* — Fish & Tsang, LLP

(57) ABSTRACT

A method is described for determining the antioxidant power of biological fluids such as saliva, serum, plasma, urine, sweat, tears and vegetal fluids, such as fruit, vegetables, beverages derived therefrom. Said method proved to be particularly suitable when evaluating the antioxidant power of saliva, which presents particular complexities from the analytical viewpoint.

Furthermore, the present invention concerns a specific reagent and a kit for implementing said method, which comprises said reagent.

18 Claims, No Drawings

(56) References Cited

OTHER PUBLICATIONS

Guo, C. et al., "Antioxidant activities of peel, pulp and seed fractions of common fruits as determined by FRAP assay", Nutrition Research, 2003, vol. 23, pp. 1719-1726.
He, Z. et al., "Phosphors Distribution in Dairy Manures", Journal of Environmental Quality, 2004, vol. 33, pp. 1528-1534.
Hirayama, O. et al., "Evaluation of Antioxidant Activity by Chemiluminescence", Analytical Biochemistry, 1997, vol. 247, pp. 237-241.
Hirayama, O. et al., "Evalutaion of Hydroxyl Radical-Scavenging Ability by Chemiluminescence", Analytical Biochemistry, 1997, vol. 251, pp. 297-299.
Huang, D. et al., "The Chemistry behind Antioxidant Capacity Assays", Journal of Agricultural and Food Chemistry, 2005, vol. 53, pp. 1841-1856.
Humphrey, S.P. et al., "A review of saliva: Normal composition, flow and function", The Journal of Prosthetic Dentistry, 2001, vol. 85, No. 2, pp. 162-169.
Iwamoto, Y. et al., "Heterogeneity of Peroxidase Related to Antibacterial Activity in Human Partoid Saliva", Journal of Dental Research, 1972, vol. 51, No. 2, pp. 503-508.
Jimenez-Escrig, A. et al., "Guava Fruit (*Psidium gujava* L.) as a New Source of Antioxidant Dietary Fiber", Journal of Agricultural and Food Chemistry 2001, vol. 49, pp. 5489-5493.
Kohen, R. et al., "Overall Low Molecular Weigh Antioxidant Activity of Biological Fluids and Tissues by Cyclic Voltammetry", Methods in Enzymology, 1999, vol. 300, pp. 285-296.
Kou, F. et al., "Hydrogen Peroxide-Induced Luminescence and Evolution of Molecular Oxygen in Human Saliva", Archive of Oral Biology, 1995, vol. 40, No. 1, pp. 15-21, Great Britain.
Magalhaes, L.M. et al., "Methodological aspects about in vitro evaluation of antioxidant properties", Analytica Chimica Acta, 2008, vol. 613, pp. 1-19.
Meyle, J. et al., "Assay of Ascorbic Acid in Human Crevicular Fluid From Clinically Healthy Gingival Sites by High-Performance Liquid Chromatography", Archive of Oral Biology, 1990, vol. 35, No. 4, pp. 319-323.
Moore, S. et al., "Antioxidant Activity of Saliva and Periodontal Disease", Free Radical Research, 1994, vol. 21, No. 6, pp. 417-425.
Nagler, R.M. et al., "Characterization of the Differentiated Antioxidant Profile of Human Saliva", Free Radical Biology & Medicine, 2002, vol. 32, No. 3, pp. 268-277.
Percival, R.S. et al., "Flow Rates of Resting Whole and Stimulated Parotid Saliva in Relation to Age and Gender", Journal of Dental Research, 1994, vol. 73, No. 8, pp. 1416-1420.
Pulido, R. et al., "Antioxidant Activity of Dietary Polyphenols As Determined by a Modified Ferric Reducing/Antioxidant Power Assay", Journal of Agricultural and Food Chemistry, 2000, vol. 48, pp. 3396-3402.
Thomas, E.L. et al., "Antibacterial Activity of Hydrogen Peroxide and the Lactoperoxidase-Hydrogen Peroxide-Thiocyanate System against Oral Streptococci", Infection and Immunity, 1994, vol. 62, No. 2, pp. 529-535.

* cited by examiner

METHOD FOR DETERMINING THE ANTIOXIDANT POWER OF BIOLOGICAL OR VEGETAL FLUIDS

FIELD OF THE INVENTION

The present invention concerns a method for determining the antioxidant power of biological fluids, such as saliva, serum, plasma, urine, sweat, tears and fluids from plants such as fruit and vegetables, and beverages derived therefrom. Said method has proved to be particularly suitable when evaluating the antioxidant power of saliva, which presents particular complexities from the analytical viewpoint.

The present invention also concerns a kit for implementing said method.

STATE OF THE ART

Saliva is the first biological fluid to be in contact with the external environment, when food, beverages or volatile substances are consumed. Its appearance is a clear, slightly acidic mucoserous-type fluid, which forms by secretions of the major glands (parotid, submandibular and sublingual) combined with gingival crevicular fluid.

The amount of saliva produced over a 24 hour period varies from 1 to 1.5 liters. Salivary flow during sleep is substantially negligible, and during waking hours while at rest it is averagely 0.3 ml/min, while under stimulation it can reach up to 7 ml/min.

Salivary flow is subjected to many variations and indeed not only circadian but also seasonal rhythms are observed, it being lower in summer and higher in winter. Flow also varies according to hydration state, age, gender (females have both baseline and stimulated secretions lower than males [1]), light intensity (there is a 30-40% reduction in darkness [2]) and certain habits such as smoking, which increases secretion in accordance with local irritation [2], and chewing gum use. The contribution to total secretion by the various salivary glands at rest (hence not stimulated by food and/or mastication) is 20% parotid, 65% submandibular and 7-8% sublingual.

However during stimulation, the predominant secretion is clearly parotid and contributes about 50% of the secretion.

In general, the saliva pH varies from 6 to 7, however, under conditions of decreased flow, pH is reduced to 5.3 whereas with an increased flow it rises to 7.8 [1]. As a general rule, parotid saliva has a higher content of amylase, proline-rich proteins and agglutinin, with small amounts of lysozyme and glycoproteins. The sublingual and submandibular glands instead produce mucines (MG1 and MG2) and lysozyme in particular.

Saliva has mainly five main functions, namely: lubrication and protection, buffering and clearance, maintenance of tooth integrity, antibacterial action and finally identification of flavours and digestion. Obviously, all these functions cannot be considered separately but form part of an integrated system [3], i.e. the saliva itself, with one of these functions being its antioxidant action. This latter function depends both on salivary flow and the types of certain saliva components.

With regard to the different types of secretions, the most considerable contribution to the water-soluble antioxidants is by the parotid, whereas others such as the lipophilic antioxidants are mostly of submandibular and sublingual origin. On the whole most secreted antioxidants are hydrophilic in nature, while other types contribute less than 10% of total antioxidant capacity [5]. In terms of antioxidants, therefore, salivary secretion comprises various compounds and enzymes, the most important of which are uric acid (UA) and the peroxidases (PDXs), both being water-soluble.

UA represents about 70% of salivary antioxidant capacity, while the other water-soluble antioxidant contained therein, i.e. ascorbic acid, appears to be of secondary or auxiliary importance compared to UA [5]. However, the concentrations of ascorbic acid in crevicular fluid appear to reach 3 times those in plasma [6]. There is a correlation between plasma and salivary UA, the plasma source prevailing.

With regard to enzymes, the most important are the PDXs. However, other enzymes have also been isolated such as glutathione peroxidase (glu POx) and superoxide dismutase (SOD) [7]. These latter are enzymes that support the production, consumption and regeneration of reduced glutathione (GSH), which is among the most important antioxidant system in the body; it operates in all cells being present in practically all fluids and therefore also in saliva though in limited amounts.

In weight terms, the PDXs represent only 0.01% of total salivary proteins, there being essentially two: the actual salivary peroxidase (PDX) and the myeloperoxidase. This latter is similar to the lactoperoxidase produced by lymphocytes in inflamed regions of the oral cavity [8, 9]. The PDXs have a double role:

a) control of $H_2O_2$ levels produced by bacteria and leucocytes;

b) antibacterial action specific for certain bacteria.

$H_2O_2$ is a potent oxidant (with the ability to cross any cell membrane) and is toxic both locally and in the gastrointestinal system. Indeed, it is able to oxidize the thiocyanate ion ($SCN^-$, i.e. the detoxification product of cyanide [$CN^-$] secreted by the salivary glands) according to the following reaction:

$$SCN^- + H_2O_2 \longrightarrow HOSCN + H_2O$$

Hypothiocyanous acid

HOSCN and its conjugate $OSCN^-$ have considerable cytotoxic capability [9] in that they are potent oxidants with antibacterial action [10]; they inhibit bacterial glycolysis by oxidizing the sulphydryl groups thereof.

On the whole, the combination of PDX, lactoperoxidase and $H_2O_2$, and $SCN^-$ is more potent than $H_2O_2$ alone [9] as it can function within a wider pH range.

Indeed, in an acidic environment the protonated form HOSCN is more active (becoming more lipophilic), whereas $H_2O_2$ is more active at neutral pH [10]. Not to be overlooked is the fact that in the reaction between $H_2O_2$ and $OSCN^-$, $\Sigma O_2$ (singlet oxygen) is also produced in part which also has considerable oxidizing power [11].

Another reaction involving $H_2O_2$ is with chlorine to form HClO (hypochlorous acid); this reaction takes place in neutrophils by the action of myeloperoxidases and is one of the bactericidal mechanisms which can act against bacterial flora.

However, oxidative processes can be either protective or detrimental, and must therefore be controlled in order to best exploit its protective potential.

From the aforedescribed it comes that the antioxidant power of saliva derives from various complex components which are difficult to evaluate. Nevertheless, a comprehensive analysis of their combined activity is an important indicator in determining the salivary defence capacity.

Table 1 below shows some of the salient salivary parameters under resting and stimulated conditions [7], to be related to antioxidant protection.

TABLE 1

Salivary flow and values for some salivary variables relating to antioxidant power at rest and after stimulation (mean values ± SD)

| Variable | Unity of measurement | Whole saliva | |
|---|---|---|---|
| Flow at rest ml/min | ml/min | 0.42 ± 0.07 | |
| Flow after stimulation | | $0.92^{a}$ ± 0.11 | |
| | | [C] | [T]* |
| POX at rest mU/ml | mU/ml | $284^{a}$ | 120 |
| POX after stimulation | | 175 | 161 |
| SOD at rest U/ml | U/ml | 0.79 | 0.33 |
| SOD after stimulation | | 0.82 | 0.74 |
| Uric acid (UA) at rest | mg/dl | $2.87^{a}$ | 1.20 |
| Uric acid (UA) after stimulation | | 1.15 | 1.06 |
| TAS at rest | mM | $0.68^{a}$ | 0.28 |
| TAS after stimulation | | 0.42 | 0.38 |
| Thiol groups at rest | μM | $26.6^{a}$ | 11 |
| Thiol groups after stimulation | | 19.1 | 18 |

*[C] concentrations; [T] total amount derived from the product of salivary flow and concentration; standard deviations of C are not shown but are available in [7];
[a]ANOVA $p < 0.05$ at rest Vs after stimulation.
TAS = total antioxidant status.

The values relate to 19 apparently healthy subjects [7] aged 18 to 54 years. Saliva was collected using a Carlson-Crittenden cup for parotid saliva while gentle suction was used for sublingual and submandibular salivas.

Stimulation was achieved with a 2% citric acid solution applied in drops (1 ml) to the tongue dorsum at 30-second intervals. The collection was made over a few minutes using both methods but the precise time period was not specified.

To be noted is that the condition of oxidative balance was expressed as SOD (superoxide dismutase enzyme), PDX (peroxidase), UA, TAS (total antioxidant status) and also, finally, by the thiol group complex (i.e. sulphur amino acid/peptide/protein groups with reducing capability).

Also to be noted is the [T] value on the right hand side of the column, i.e. the product of flow and concentration. This value was not given by the authors but is derived by suitably processing the data to thus allow a more complete examination of what is taking place.

From this evaluation of T, it follows that, while the concentrations tend to decrease on stimulation (except for SOD), the total amounts of all the components tend to increase (PDX by 34%, SOD by 124%, TAS by 36%, thiol groups by 50%) except for UA which tends instead to decrease.

Therefore, it would seem that the predominant antioxidant in saliva cannot be expressed as concentration but should be expressed as total amount. Moreover, the total antioxidant power, expressed as TAS should also be expressed as total capacity and not as concentration, in order to achieve a more precise measurement.

In another study [5], on 28 apparently healthy subjects aged between 25 and 50 years, shown in table 2, the antioxidant power of saliva was determined by evaluating the TAS (total antioxidant status or capacity TAC or activity TAA). In this experiment saliva was collected in a different manner than the previous experiment and over a 15 minute period. For the collection at rest, the subjects simply spat into a container whereas under stimulated conditions the collection was carried out by chewing 1 g of paraffin then making the subjects spit into suitable containers every 2 minutes for 15 minutes.

TABLE 2

Salivary flow and values for some salivary variables relating to antioxidant power at rest and after stimulation (mean values ± SD)

| Variable | Unity of measurement | Values | Total [T]* |
|---|---|---|---|
| Flow at rest | ml/min | 0.33 ± 0.17 | |
| Flow after stimulation | | 1.93 ± 1.07 | |
| TAS at rest | mM | 0.25 ± 0.06 | 0.08 |
| TAS after stimulation | | 0.14 ± 0.04 | 0.28 |
| Uric acid at rest | mg/dl | 3.68 ± 0.64 | 1.21 |
| Uric acid after stimulation | | 1.75 ± 0.36 | 3.40 |
| Albumin at rest | μM | 12 ± 7 | 4.10 |
| Albumin after stimulation | | 8 ± 2 | 15.40 |
| Ascorbate at rest | μM | 9 ± 6 | 3.00 |
| Ascorbate after stimulation | | 9 ± 4 | 17.00 |

*[T] the product of concentration and flow

As in the case of Table 1, the product of flow and concentration calculations [T] are given in units comparable with those of the values in table 1. As with the previous study, it can be seen that stimulation reduces the concentrations but increases the total amounts.

The other important element which raises is represented by the differences in flow (both resting flow and stimulated flow) which behave as either negative or positive "amplifiers" of the total amounts.

In this respect, a flow reduction from 0.42 ml/min (Table 1) to 0.33 ml/min (Table 2) [corresponding to an approximately 20% reduction] results in a modification of the total amount of TAS from 0.28 mM (Table 1) to 0.08 mM (Table 2) corresponding to an approximately 70% reduction of TAS. The differences are further amplified in proportion to stimulation of the flow; as the flow increases by 2-fold so the total TAS increases 8-fold.

From the examples shown it comes that estimation of the actual TAS should be carried out on standardized flows, possibly limited to avoid excessive amplifications.

In the same experiment, see Table 3 below, some cases of paradontosis were considered for which the essential disease criteria were not outlined (cases with a mild to moderate degree of paradontosis, with poor oral hygiene).

TABLE 3

Salivary flow and values for some salivary variables relating to antioxidant power at rest and after stimulation (mean values ± SD) Subjects with paradontosis (mean values ± SD) on 7 cases (4 F, 3 M aged between 25 and 45 years)

| Variables | Unity of measurement | Values | Total [T] |
|---|---|---|---|
| Flow at rest | ml/min | 0.34 ± 0.17 | |
| Flow after stimulation | | 1.33 ± 0.58 | |
| TAS at rest | mM | 0.30 ± 0.01 | 0.10 |
| TAS after stimulation | | 0.17 ± 0.07 | 0.23 |
| Uric acid at rest | mg/dl | 4.27 ± 0.89 | 1.45 |
| Uric acid after stimulation | | 2.20 ± 0.06 | 2.90 |
| Albumin at rest | μM | 11.7 ± 7.0 | 4.00 |
| Albumin after stimulation | | 9.3 ± 2.8 | 12.40 |
| Ascorbate at rest | μM | 6.4 ± 3.6 | 2.10 |
| Ascorbate after stimulation | | 6.6 ± 2.9 | 8.80 |

The authors conclude that:

a) the saliva of the subjects affected by paradontosis has an antioxidant power identical to that of normal subjects;

b) the UA correlates well with the antioxidant power of saliva.

Actually, by considering the T values and comparing the values with those in table 1, it can be seen that:

i) salivary stimulation in normal subjects increases TAS 3.5-fold, while in subjects with paradontosis the increase is 2.5-fold (70% lower);

ii) salivary stimulation in normal subjects increases UA 2.8 fold, while it increases only 2.0 fold in cases with disease (70% lower); the same can be said for ascorbate (lower by 70%); for albumin the differences are 20% lower.

In other words, under these experimental conditions exactly the opposite has been demonstrated, i.e. that the antioxidant defences of the subjects affected by paradontosis are reduced, a fact which has been recently extensively demonstrated [12].

The systematic evaluation of the antioxidant power of saliva dates back to the end of the 1990's, actually resorting to using the same methods as used for serum or plasma [13, 14, 15].

For the most part, these methods focussed on researching single components, such as PDXs, UA, GSH, vitamins, or researching oxidative adducts, such as isoprostanes, TBARS (thiobarbituric reactive substances), MDA (malonyldialdehyde) and hydroperoxides.

The known methods which instead evaluate antioxidant capacity in its entirety are of three different types: spectrophotometry, chemiluminescence and voltametry.

Spectrophotometric methods are identical to those used for the determination in blood and exploit the principle of radical-type substance reactivity.

These substances are extremely reactive and tend to bind immediately to an acceptor which captures them then changes colour following their capture. The antioxidants (which have reducing power) contained in the fluid to be evaluated will tend to give up their electrons to the radical-type substances which were purposely added to the sample in known amounts; the acceptor will hence be unable to capture them. In this manner the extent of colouration will be reduced.

The usual acceptor [5] is 2,2'azinobis (3-ethylbenzthiazoline 6 sulphonate) i.e. ABTS, which upon capturing the radical is transformed into radical ion $ABTS^{+}$ becoming blue-green in colour. Readings are made in the UV region, but also at 660 nm, 734 nm, and 820 nm. Normally, methemoglobin is used as the oxidizable product, and $H_2O_2$ is used as oxidizing product. The combination of the two products in the fluid generates a Fenton reaction and the radical that forms ($OH^{\bullet}$) is captured by ABTS which is transformed into $ABTS^{+}$.

Usually with this type of reaction, reference is made to a standard solution with a known antioxidant power. The most used system is one that refers to trolox, i.e. to a soluble analogue of vitamin E.

Therefore, the antioxidant potential is expressed as TEAC (i.e. Trolox Equivalent Antioxidant Capacity); the values which result from this method are termed, according to the authors, TAC (total antioxidant capacity), or TAA (total antioxidant activity) or TAS (total antioxidant status). The reactive variables, partly modified to improve the method, are such that values obtained with the same method are often very different even in the case of controls.

Therefore, the comparisons are only reliable for experiments conducted under the same experimental conditions, i.e. the data originating from different laboratories are poorly comparable.

The second method is based on chemiluminescence [13, 15].

HRP (horseradish peroxidase) catalyzes the oxidation of luminol with $H_2O_2$. The light produced by the reaction is amplified in the presence of p-iodophenol in the reaction which intensifies the light signal.

This signal can be reduced by the presence of antioxidants in the fluid and the reduction remains until the antioxidants are exhausted. The antioxidant capacity is parametrized with a standard curve using a known antioxidant.

A further method, based on this same principle exploits the capacity of the antioxidants present in the fluid to inhibit the luminescence generated by contact between hydroperoxides (which are oxidized products and hence indirect indicators of oxidation) with isoluminol/myeloperoxidase [14].

The Fenton reaction can also trigger a chemiluminescent stimulus, due to formation of a $OH^{\bullet}$ radical which can be reduced if antioxidants are present depending on the fluid in which the reaction is triggered [16]. However, this method proved to be poorly reproducible, in that different laboratories gave different results which were not very comparable, even on healthy individuals [13, 15].

The third type is based on cyclic voltammetry [17] which is sensitive to the presence of low molecular weight antioxidants in saliva. The sample to be evaluated is placed in a cuvette containing three electrodes; the supporting electrode (carbon), the reference electrode (Ag/AgCl) and the auxiliary electrode (Pt). The application of a constant potential to the reference electrode enables a potential (cyclic voltammogram) to be recorded whose value is a function of the capacity of the antioxidants contained in the fluid to donate electrons.

However, not all antioxidants are able to donate electrons in an amount detectable by the reference electrode; therefore the measurement is only a partial one such that recourse must sometimes be made to electrodes specific for certain antioxidants (of GSH type).

Also known is the FRAP (Ferric Reducing/Antioxidant Power) test, established for the first time by Benzie and Strain (1999) for measuring the reducing power of plasma, then adapted to assay the antioxidant capacity of botanical species. The test measures the reduction of ferric 2,4,6-tripiridyl-s-triazine (TPTZ) to form an intense blue product (Guo et al, 2003; Jimenez-Escrig et al., 2001). The reducing power is related to the degree of hydroxylation and extent of conjugation in the polyphenols (Pulido et al., 2000). However, the FRAP test is unable to detect compounds that act by hydrogen transfer (radical quenching), such as thiols and proteins. This leads to underestimation of the results, particularly in serum. Moreover, the strongly acidic pH, which is used in the FRAP test for maintaining iron in solution, leads to a shift in the dominant reaction mechanism with the consequent implication that the FRAP test results are not comparable with other measurements of antioxidant tests. The FRAP is founded on the premise that redox reactions take place rather rapidly (in 4 to 6 minutes) but actually this does not happen at any time. This makes this test strongly dependent on the time taken for the analysis.

Also known is the BAP (biological antioxidant potential) test which evaluates the antioxidant power of plasma serum in terms of the capacity of the latter to reduce ferric ions to ferrous ions, and detects the colour changes of a suitable chromogen by means of photometry.

In the BAP test, therefore, the serum sample to be analyzed is dissolved in a coloured solution obtained by adding a source of ferric ions ($FeCl_3$, i.e. ferric chloride) to a specific chromogen (a sulphur based compound). After a brief incubation (5 minutes), the solution decolourizes; this decolouration will be more pronounced the more the components of the tested serum will have been able to reduce the ferric ions initially present and responsible for forming the coloured complex in the considered time interval. By photometrically evaluating the extent of this decolouration, it is possible to measure the amount of reduced ferric ions and, in short, the reducing ability or antioxidant power of the tested serum relative to a reference serum, known as the calibrator. The test results, i.e. the iron-reducing "physiological" antioxidant power of the serum, are expressed in mEquivalents of antioxidants that reduce ferric iron per liter of sample, according to the formula:

$$\frac{[\text{Abs blank reagent} - \text{Abs sample}]}{[\text{Abs blank reagent} - \text{Abs calibrator}]} \times [\text{calibrator}]$$

where:

[Abs] are the absorbance values of the solution measured at 505 nm; and

[calibrator] is the calibrator concentration expressed in mEq/1.

Bearing in mind that 1 ml of serum is considered sufficient to reduce at least 1.8 μmol/l of vitamin C, the results of the BAP test are then compared with the following reference table:

| Reference values expressed as μmol/l of antioxidant substances such as vitamin C | |
|---|---|
| >2200 | Optimal value |
| 2200-1800 | Borderline value |
| 2000-1800 | State of moderate deficiency |
| 1800-1600 | State of deficiency |
| 1600-1400 | State of severe deficiency |
| <1400 | State of very severe deficiency |

The BAP test has been declared to be linear between 1000 and 3000 μmol/l.

However, it has been noted that this test, as well as being depending on the use of said calibrator of unknown provenance and type, does not account for the composition complexity of the samples to be analyzed, particularly in the case of biological fluids, where compounds are present which interfere with the reduction of ferric ions, thus altering and falsifying the determination of the resulting antioxidant power in respect of its actual value, hence leading to an incorrect evaluation of the actual antioxidant state of the sample.

From what aforestated with respect to the discussion of the dedicated literature on the matter, the object of the present invention is hence to identify a method that enables the level of antioxidant power in biological and vegetal fluids to be evaluated reliably, reproducibly, repeatedly and economically, overcoming in this manner the above stated disadvantages regarding to the known methods.

SUMMARY OF THE INVETION

The aforementioned object has been achieved by means of a reagent for determining the antioxidant power of biological and vegetal fluids comprising at least one inorganic zirconium salt and at least one suitable solvent, as indicated in claim 1.

Another aspect of the invention concerns a method for determining the antioxidant power of biological and vegetal fluids as indicated in claim 6.

Another aspect of the invention concerns a kit for implementing said method as indicated in claim 17.

The characteristics and advantages of the present invention will be evident from the detailed description given below, as well as the working examples provided for illustrative and non-limiting purposes.

DETAILED DESCRIPTION OF THE INVENTION

Both the reagent and method of the present invention, by starting from the principle underlying the BAP test used for evaluating the antioxidant power of solely plasma, have, as will be seen extensively hereinafter, surprisingly enabled all the known disadvantages associated not only with said BAP test but also the aforementioned methods of the known art to be overcome, while at the same time achieving absolutely unexpected additional advantages.

As already mentioned, starting from the BAP test, which is based on a capacity to inhibit the reaction between thiocyanate (SCN) and $Fe^{3+}$, the inventor has firstly studied the distinctive characteristics of the methodology of said test in order to collect information on the results which this latter is able to provide. Said information was then used in a comparison with the results obtained with the method of the invention, in order to prove its effectiveness and the significant improvements in all the considered aspects.

As is known, thiocyanate ($SCN^-$) reacts with $Fe^{3+}$ to generate the ferrothiocyanate complex ($Fe[(SCN)_6]^{3-}$); this complex is reddish brown in colour and is detected by UV-Vis spectrophotometer at a wavelength of 505 nm. The reducing substances, within the fluid sample to be evaluated, reduce $Fe^{3+}$ to $Fe^{2+}$ thus removing it from the reaction with thiocyanate and hence modifying sample absorbance.

The inventor of the present invention has surprisingly found that the compounds which interfere with ferric ion reduction, thus altering the resulting antioxidant power determination with respect to its actual value, and hence indeed leading to an incorrect determination of the actual antioxidant state of the sample, are the phosphates in the biological and vegetal fluid samples.

In particular, the inventor has noted that saliva, for example, has a phosphate content varying from 1 to over 50 mg/100 ml, whereas in serum the amount is from 2.6 to 4.5 mg/100 ml. Therefore, as these amounts of phosphates are absolutely not negligible, the cause underlying the totally inaccurate and imprecise measurements of antioxidant power with the BAP test such as to produce actual false positives, can be understood.

A further problem that arises in order to achieve a determination of antioxidant power as repeatable and reproducible as possible, particularly if the biological fluid to be analyzed is saliva, is to standardize salivary flow in terms of ml/min because, as aforesaid, the antioxidant power varies in an indirectly proportional way to the flow itself. The inventor of the present invention has surprisingly found that for a flow of 0.70 ml/min to 1.50 ml/min the concentrations by which the antioxidant power is evaluated are not only comparable but also actually matching, as will be widely explained and demonstrated in Example 2 and Example 3 to follow.

The invention therefore provides a reagent for determining the antioxidant power of biological and vegetal fluids comprising at least one inorganic zirconium salt and at least one suitable solvent. In this respect, the use of said reagent enables the presence of phosphates in the biological and vegetal fluid sample to be masked, thus advantageously avoiding that said phosphates interfere with the antioxidant power determination while at the same time maintaining them in solution, i.e. avoiding a precipitation which would disadvantageously result in a dedicated separation step. This result is extremely important for diagnostic purposes, in particular when the biological fluid to be analyzed is saliva, wherein the equilibrium of remineralization/demineralization of enamel can generate, as stated, phosphate amounts of even >50 mg/dl, compared to which the BAP test proves to be totally unreliable for determining the real antioxidant power of saliva, even overestimating the results by 57% as evaluated in Example 4. With regard to serum, the average phosphate amount does not exceed 4.5 mg/dl under normal conditions. Despite this, the values for total antioxidant power determined by BAP were overestimated by 33%, as again evaluated in Example 4.

Therefore, the masking action of phosphates on $Fe^{3+}$, as seen and studied by the inventor of the present invention, should be considered each time the determination of antioxidant power of a fluid is of interest (see also FRAP test [21]). From this it can be appreciated how surprising and advantageous is the selection of inorganic zirconium salts for the reagent of the invention.

Preferably, in said reagent, said inorganic zirconium salt is chosen from the group consisting of fluoride, chloride, bromide, iodide, carbonate, sulphate, nitrate and mixtures thereof. More preferably, said inorganic zirconium salt is chosen from the group consisting of fluoride, chloride, bromide, iodide and mixtures thereof.

According to a preferred embodiment, said inorganic zirconium salt is $ZrCl_4$.

Preferably, said at least one suitable solvent is a water-lower alcohol mixture, where lower alcohol means a linear or branched ($C_1$-$C_5$)alcohol. More preferably, it is a water-($C_1$-$C_3$)alcohol mixture. According to a preferred embodiment, said solvent is a water-isopropyl alcohol mixture. Preferably, said reagent further comprises a thiocyanate salt, more preferably a thiocyanate inorganic salt with an alkali metal or an alkaline earth metal.

In a further aspect, the present invention relates to the use of said reagent for determining the antioxidant power of biological and vegetal fluids, as widely demonstrated also in the given Examples.

Another aspect of the present invention concerns a method for determining the antioxidant power of biological and vegetal fluids, comprising the steps of:

a) providing an alcoholic solution of thiocyanate;

b) adding at least one reagent as aforedescribed;

c) adding an aqueous ferric salt solution;

d) measuring the absorbance of the thus obtained solution;

e) adding the biological or vegetal fluid sample;

f) measuring the absorbance of the solution containing the sample;

g) subtracting the absorbance at step d) from absorbance at step f); and h) plotting the absorbance value thus obtained on the standard calibration curve of vitamin C and obtaining a value for the antioxidant power as vitamin C equivalents, according to Lambert-Beer's law, of the fluid under examination.

For the purposes of the present invention, by the term "biological or vegetal fluid" it is meant any fluid of animal or vegetal origin, such as saliva, serum, plasma, urine, tears, sweat, fluids derived from fruit, vegetables, foods, wine, beer, beverages, coffee, tea. Preferably said biological fluid is saliva, serum, plasma, urine, or tears.

It has been surprisingly and advantageously observed that, by using the aforedescribed reagent, the antioxidant power of biological and vegetal fluids can be determined by acquiring the absorbance of the sample, in a rapid, very simple, repeatable and reproducible manner, since the interference caused by the phosphates is completely and effectively excluded. Furthermore, the method of the present invention advantageously requires no additional reference substances, such as a calibrator, which in the BAP test is essential and necessary for serum, though of unknown provenance and type.

Preferably, said calibration curve is already preset in the UV-Vis spectrophotometer, and so automatically supplies a value for antioxidant power of the fluid in question as vitamin C equivalents (μmol/l). Indeed, as will be seen more extensively in Examples 1A-1D to follow, the calibration curve of vitamin C has proved to be extremely stable, even after variations in ferric salt concentrations and/or variations in zirconium salt concentrations.

Preferably, said ferric salt is chosen from the group consisting of fluoride, chloride, bromide, iodide, carbonate, sulphate, and nitrate. According to a preferred embodiment said ferric salt is nitrate.

Preferably, said inorganic zirconium salt of the reagent b) and said ferric salt are in a molar ratio of from 20:1 to 5:1. More preferably, said inorganic zirconium salt and said ferric salt are in a molar ratio of from 15:1 to 8:1. According to a preferred embodiment, said inorganic zirconium salt and said ferric salt are in a molar ratio of about 10:1.

These molar ratios hence mean an excess of zirconium with respect to the $Fe^{3+}$ ion, as this significantly facilitates the task of effectively masking the phosphates by zirconium salts, as well as maintaining them in solution and preventing their precipitation, as will also be seen in Example 6.

Preferably, said sample of biological or vegetal fluid and the solution obtained after step c) are in a volumetric ratio of from 1:250 to 1:50. More preferably, said sample of biological or vegetal fluid and the solution obtained after step c) are in a volumetric ratio of from 1:180 to 1:75. Even more preferably, said sample of biological or vegetal fluid and the solution obtained after step c) are in a volumetric ratio of from 1:120 to 1:90.

These ratios were actually found to increase the probability that the volumetric strength determination fell directly within the limits set for the calibration curve of vitamin C (500-6000 μmol/l) without needing further dilutions.

With regard to the volumes of biological or vegetal fluid samples, since the analysis is conducted in a UV-Vis spectrophotometer, volumes suitable for introduction into a cuvette are considered. In this regard, it was noted that for saliva, tears, and sweat volumes of about 5 μl are preferred, for blood (serum or plasma) 10 μl, while for urine 10 μl, but after having been diluted 1:5 with deionized $H_2O$.

Another aspect of the present invention concerns a kit for implementing the aforedescribed method, comprising:

i) at least one reagent as aforedescribed;

ii) at least one alcoholic thiocyanate solution;

iii) at least one aqueous solution of a ferric salt; and iv) an illustrated leaflet comprising the instructions for carrying out the antioxidant power determination.

The advantageous result has been to significantly simplify the components needed for the determination of antioxidant power of biological or vegetal fluids in that, in contrast to the BAP test, the kit of the invention absolutely does not comprise a calibrator, i.e. reference serum. Indeed, as the method of the present invention refers directly to the calibration curve of vitamin C, there is no need for a reference sample, neither for serum nor for any other fluid, hence achieving a series of remarkable advantages including better repeatability, better reproducibility, reduced cost and excellent reliability of the results as will be also demonstrated in the following examples, particularly Examples 4 and 5.

Preferably, said i) at least one reagent and said ii) at least one alcoholic thiocyanate solution are a single solution (1).

In a preferred embodiment, said illustrative leaflet further comprises instructions for collecting the biological and vegetal fluid sample. More preferably when said biological fluid is saliva, said further instructions for sample collection indicate that said collection is carried out under conditions of said salivary flow being of 0.70 to 1.50 ml/min. Even more preferably, said further instructions for sample collection indicate that said collection is carried out under conditions of said salivary flow being of 1.00 to 1.30 ml/ml. In a preferred embodiment, said salivary flow is about 1.20 ml/min.

It should be understood that all aspects identified as preferred and advantageous for the method of the invention are also to be considered similarly preferred and advantageous for the kit and the use thereof.

Working examples of the present invention are hereinafter provided for illustrative and non-limiting purposes.

EXAMPLES

Example 1

Method for Determining the Antioxidant Power of Saliva, Plasma and Urine, According to the Present Invention The following components were prepared:

| | | Amount | Volume |
|---|---|---|---|
| Sample | | | 10 µl |
| Solution (1) | isopropyl alcohol | | 600 µl |
| | demineralized $H_2O$ | | 355 µl |
| | $ZrCl_4$ | 47.20 mmol | 5 µl |
| | KSCN | 0.11 mmol | 10 µl |
| Solution (2) | $Fe(NO_3)_3$ | 5.01 mmol | 30 µl |
| Total | | | 1010 µl |

Solution (1) was prepared by combining the zirconium chloride solution and the alcoholic thiocyanate solution; this solution (1) was then introduced into a cuvette for spectrophotometric UV-Vis analysis. Solution (2) was then added, thus turning the colour from transparent to reddish-brown, whose intensity was proportional to the presence of $Fe^{3+}$ reacted with thiocyanate. Immediately after, the wavelength corresponding to the maximum peak of absorbance measured by spectrophotometer was identified as being in this case 505 nm.

Subsequently, the sample was also added to the cuvette. After 5 minutes, the absorbance reading was repeated. The difference between the first and second absorbance readings enabled the concentration to be obtained in terms of µmol/l of vitamin C, by means of Lambert-Beer's law, and hence the antioxidant power of the tested sample.

In this respect, vitamin C was used as a standard for calibrating the method, as it showed linear values between 500 and 6000 µmol/l, as demonstrated in Example 1A to follow. For concentrations >6000 µmol/l, the sample was suitably diluted with deionized water, until its values fell within 500 and 6000 µmol/l of vitamin C.

Example 1A

Linearity of the Method of the Present Invention

The aim of Example 1A was to demonstrate the linearity of the determination of the method of the invention between the values 500 and 6000 µmol/l of vitamin C, which was used as a reference to determine the antioxidant power of the relevant fluids.

Firstly, it was noted that the maximum absorbance value of solutions (1) and (2) together, as in Example 1, corresponded to a concentration of 7134±67.7 µmol/l with CV<1% (where CV is the coefficient of variation). This value was obtained by subtracting the blank reading, i.e. of solution (1) alone, from the reading of solutions (1) and (2) together.

To develop the calibration curve as a function of the scalar amounts of vitamin C, different solutions of vitamin C were prepared, at scalar concentrations starting from 500 µmol/l with multiplier (2, 4, 8, 10, 12) obtained by diluting with demineralised water vitamin C in a concentrated solution (35.22 mg/ml) in demineralised water. The determinations were carried out 5 times for each dilution, the measurements being taken with different successions; for half the samples, with increasing concentrations (from 500 to 6000 µmol/l) and for the other half with decreasing concentrations (from 6000 to 500 µmol/l). All the measurements were carried out during the same day under temperature controlled conditions (25° C.).

The values were analyzed statistically by applying Student's t-test between the actual determinations and expected values; all the data are given in Table 4.

TABLE 4

Determinations for different vitamin C concentrations. Mean values ± SD of 5 determinations

| | Vitamin C concentrations (µmol/l) | | | | | | |
|---|---|---|---|---|---|---|---|
| Variables | 500 | 1000 | 2000 | 4000 | 5000 | 5500 | 6000 |
| Actual data (µmol/l) | 505 ± 16.2 | 1007 ± 35.7 | 2020 ± 65.7 | 4036 ± 129.0 | 5046 ± 161.5 | 5556 ± 176.9 | 6196 ± 186.0 |
| CV (%) | 3.2 | 3.5 | 3.3 | 3.2 | 3.3 | 3.2 | 3.0 |
| Expected data (µmol/l) | | 1009 ± 32.4 | 2018 ± 64.8 | 4037 ± 129.6 | 5046 ± 162.0 | 5550 ± 178.2 | 6055 ± 194.3 |
| t- Test for independent data (t values) | | 0.921* | 0.974* | 0.989* | 0.998* | 0.960* | 0.276* |

*t-test for interdependent actual data Vs expected data: $p > 0.05$

As can be seen from the analysis of the data given in Table 4, the calibration curve is perfectly linear, i.e. is actually a straight line up to values of 6000 μmol/l with CV varying from 3.0% to 3.5%.

Example 1B

Evaluation of the Effect of the Ferric Salt Amount on the Vitamin C Calibration Curve This example was undertaken to demonstrate that different amounts of ferric salt in solution (2) did not give rise to significant alterations in determining the μmol/l values of vitamin C.

For this purpose the determination was undertaken on the same samples as Example 1A, utilizing solely the standard vitamin C concentrations of 2000 and 4000 μmol/l and adding three different volumes of the same $Fe(NO_3)_3$ concentration, i.e. 25 μl-30 μl-35 μl.

The analysis of variance (ANOVA) was calculated on the data.

The results are shown in Table 5.

TABLE 5

Determinations on two vitamin C concentrations with added $Fe(NO_3)_3$ at different volumes. Mean values ± SD on 5 samples

| | Volumes of $Fe(NO_3)_3$ | | | |
|---|---|---|---|---|
| | 25 μl | 30 μl | 35 μl | ANOVA |
| 2000 μmol/l | 2023 ± 58.0 | 2020 ± 65.7 | 2026 ± 63.5 | p > 0.05 |
| 4000 μmol/l | 4041 ± 123.1 | 4036 ± 129.0 | 4043 ± 130.2 | p > 0.05 |

This test confirmed that no significant variations were seen when using volumes between 25 and 35 μl of $Fe(NO_3)_3$ at the same concentration.

Example 1C

Evaluation of Possible Interference by Zr Salts on the Calibration Curve of Vitamin C The example was undertaken to demonstrate that inorganic Zr salts did not interfere with, i.e. did not alter, the linearity of the calibration curve of vitamin C.

Vitamin C was used as the comparison sample with two different solutions (1):

solution (1)-AcZ, i.e. containing Zr in the form of $ZrCl_4$, and solution (1)-AsA, i.e. without Zr.

The sample consisted of a 2000 μmol/l vitamin C solution in deionized water. The vitamin C solution was prepared 10 times in succession; for each vitamin C sample, the test was performed using both solutions (1) in immediate succession.

For five times, the (1)-AcZ was evaluated before the solution (1)AsZ and for 5 times after it. The $ZrCl_4$ concentration was 47.2 mmol/l and the volume introduced into the cuvette was 5 μl.

The coefficient of variation (% CV) was also evaluated on these samples.

The data were compared using the t-test for interdependent data and shown in Table 6.

TABLE 6

Determinations on a vitamin C solution at a 2000 μmol/l concentration in the presence or absence of $ZrCl_4$. Mean values ± SD.

| | Values in μmol/l of vitamin C | % CV | P |
|---|---|---|---|
| solution (1)-AsZ | 2031 ± 73.1 | 3.6 | Ns |
| solution (1)-AcZ | 2040 ± 42.2 | 2.1 | |

Ns = p < 0.05 t-test for interdependent data

It followed from the above reported data that addition of inorganic Zr salts advantageously did not modify the calibration curve of vitamin C; also, it was noted that the presence of inorganic Zr salts conveniently significantly reduced % CV.

Example 1D

Evaluation on Different Samples of Human Biological Fluids

The method of the invention was evaluated by using different amounts of different biological fluid samples.

For this purpose, samples of urine, saliva and tears were examined deriving from the same 10 subjects, all of them healthy volunteers.

Their saliva was collected in a plastic container following chewing on cotton, at an amount of >1 ml; urine was collected externally in a plastic container at an amount of 20 ml; tears were collected in a microcuvette following exposure for a very short time (3 seconds) to the gas ortho-chloro-benzal malonitrile under an extractor hood. The tears were collected in a minimum amount of 100 μl. This final determination was carried out on 5 cases only (3 males and 2 females).

The characteristics of the volunteers who participated in the research are given below (mean values±SD):

| Variables | Values |
|---|---|
| Age (years) | 23 ± 1.7 |
| Gender | 5 M and 5 F |

All the samples were analyzed on the day of collection; half of the cases were evaluated with succession from 5 μl to 10 μl, while the other half with the reverse succession.

The urine specimens were diluted in a ratio of 1:5 with deionized water.

The results are shown in Table 7.

TABLE 7

Determinations on samples of biological fluids. Mean values ± SD

| | | amounts in μl | | |
|---|---|---|---|---|
| | No. of cases | 5 | 10 | P* |
| Saliva (μmol/l) | 10 | 1127 ± 179.9 | 2250 ± 355.5 | Ns |
| Urine (μmol/l) | 10 | 2178 ± 205.9 | 4358 ± 413.4 | Ns |
| Tears (μmol/l) | 5 | 1199 ± 182.6 | 2394 ± 371.8 | Ns |

*t-test for interdependent data comparing the values for 10 μl with those for 5 μl multiplied by 2; Ns = p > 0.05

In accordance with the method of the invention, a determination of the antioxidant power of the samples was hence achieved by reading the absorbance and calculating the corresponding concentration, by means of Lambert-Beer's law, in terms of μmol/l vitamin C equivalents, after multiplying by a factor of 6.500.

Example 2

Standardizing the Amount of Saliva for Use as a Sample in the Method of the Invention When the biological fluid to be analyzed is saliva, in view of its analytical complexity, the appropriateness of standardizing its collection was considered. First of all, this collection was made subsequent to the everyday oral hygiene measures using toothpaste and/or dental floss and/or mouthwash. The saliva was collected at least one hour after said hygiene procedures.

Saliva was therefore collected by asking the subject while comfortably seated to chew some suitably prepared hydrophilic cotton in an amount of 300±30 mg for a 60 second period.

The subject on average achieved no more than 60±2 mastications without excessive compression of the cotton between the teeth, but moving it within the mouth during chewing.

When chewing was finished, the cotton was collected in a suitable container, whose weight was represented by the sum of the container weight plus that of the cotton (tare). After subtracting the tare, the extent of the fluid representing salivary flow/min was evaluated. Under optimal conditions for the method of the invention, said flow was 1.2±0.2 ml/min.

If the amount obtained was not in the region of said values, saliva collection had to be repeated after an interval of at least 5 minutes, until the desired amount was attained by modulating chewing; i.e. increasing chewing in case of low flow or reducing it in case of high flow. Should the flow be very low, this being an infrequent but possible event, the same amount of cotton could be used but with addition of a drop (45 μl) of 3% citric acid solution. In this way, almost 100% of subjects with salivary flow <0.5 ml/min were able to increase the salivary flow to levels suited to the evaluation i.e. between 0.70 and 1.5 ml/min.

The determinations following centrifugation of the saliva sample were always identical to samples not centrifuged at 800 rpm. Centrifugation, therefore, could only be useful should salivary detritus be evident in the saliva.

In view of the results obtained above by the method of the present invention, together with the expedients for the sampling in the specific case of saliva, high repeatability and reproducibility of the method were achieved as demonstrated in the following Examples 3-6.

Example 3

Impact of Salivary Flow on the Determination of Saliva Antioxidant Power According to the Method of the Invention 10 subjects were selected of both genders (5 males and 5 females) formally healthy. In this respect, the admission criteria required that they were non-smokers, did not follow any therapy, including birth control, nor were taking any food supplements.

The subjects had to present themselves as fasted from the previous night and told to avoid excess food for the entire day preceding the test, and also excessive physical exercise.

The test was carried out at a controlled temperature of 25° C. The subjects were kept under resting conditions for 30 minutes before evaluating flow and antioxidant power of the saliva.

The measurements of salivary flows were carried out according to the following method.

The seated subject had to chew on a small square of hydrophilic cotton of 300±30 mg. It was required to chew the cotton for a period of one minute without excessively compressing it between the teeth, but allowing it to move within the mouth. A rhythm of about 60 mastications/minute was required to be maintained allowing the saliva to flow into the cotton.

At the end of one minute, the cotton was expelled from the mouth and collected in a suitable plastic container of known weight. The entirety was weighed and the subtraction of the container tare and the cotton weight provided the saliva weight and hence determined the flow thereof. This evaluation was repeated after 10 minutes to gain a more precise determination of the capacity of the various subjects to produce saliva.

Depending on salivary flow, the subject was asked to modify the number of mastications and activation of saliva. If the flow was lower than 0.70 ml/min the subjects were asked to increase the number of mastications and their effort to produce saliva. If the flow was much higher than 1.50 ml/min (e.g. above 3 ml/min) the subjects were asked to reduce mastications.

If the saliva flow was too low, a solution of citric acid (45 μl of a 3% aqueous solution) could be added to increase the amount, but none of the test subjects required it.

Each subject was subjected to three run-in tests which were carried out the day before the start of the actual test.

The protocol comprised the evaluation of 5 different salivary flows, namely:

from 0.3 to 0.60 ml/min;
from 0.6 to 0.9 ml/min;
from 0.91 to 1.3 ml/min;
from 1.31 to 1.8 ml/min; and
from 1.81 to 2.5 ml/min.

This capacity for producing differentiated salivary flows was considered an admission criterion: in effect, the 10 final subjects were derived by screening 15 subjects. The rejected cases were because of scanty production (3 subjects), or difficulty in adequately stimulating salivary flow (2 subjects) i.e. flow could not be modified to the required extent.

After the run-in, the test was repeated on the same subjects three times a day (1, 3 and 5) with the aim of determining the repeatability of the data.

The sessions on the first day of evaluation were denominated "Flows 1, 2, 3, 4, 5", while those on subsequent days were denominated Flow 6 (on the third day) and Flow 7 (on the fifth day).

The first day of actual evaluation tested the antioxidant power of all five saliva flows, whereas the other two tests on subsequent days (day 2 and day 5) evaluated only those flow values that were considered ideal for the test (as will be seen below) i.e. between 1 and 1.5 ml/min.

The total antioxidant power was determined on saliva by using the method of the invention, thus operating on an amount of 10 μl of saliva.

All the data were statistically analyzed by calculating the means and dispersion parameters (SD or standard deviation) and comparisons were made on the basis of Student's t-test for interdependent data as well as analysis of variance for orthogonal contrasts.

Results

The characteristics of the 10 subjects are given below:

| Variable | Values |
|---|---|
| Gender | 5 M and 5 F |
| Age (years) | 28 ± 6.7 |
| Weight (Kg) | 67 ± 10.5 |
| Height (m) | 1.68 ± 0.083 |
| BMI* (kg/$m^2$) | 23.4 ± 1.60 |

*BMI = body mass index

All the subjects successfully completed the test. The measurements of salivary flow and relative concentrations in terms of μmol/ml of vitamin C, during the first day of monitoring the different flows, are given in Table 8 below.

Also calculated was the product of "flow×test", this being an expression of the total oxidative capacity (TC). All measurements were undertaken by using 10 μl and the values were expressed as μmol/l of vitamin C. Examination of the data showed that when the mean flow ranged from 0.75 ml/min to 1.14 ml/min the test values practically matched. Flows lower than 0.70 ml/min or higher than 1.50 ml/min showed higher or lower concentrations respectively, in both cases in a significant manner (t-test $p<0.05$). Therefore it can be concluded that by maintaining a salivary flow of 0.70 ml/min to 1.5 ml/min, the resulting concentrations in terms of μmol/l of vitamin C vary negligibly.

TABLE 8

Volumes of saliva (ml/min) and concentrations in terms of μmol/l of vitamin C. Mean values ± SD.

| Variables | Values | Total capacity (TC) [Flow × test] |
|---|---|---|
| Flow 1 | 0.43 ± 0.095 | |
| test 1 | 4316 ± 381.5 | 1846 ± 383.8 |
| Flow 2 | 0.75 ± 0.085$^a$ | |
| test 2 | 3753 ± 301.4 | 2804 ± 299.1$^c$ |
| Flow 3 | 1.10 ± 0.082$^a$ | |
| test 3 | 3492 ± 282.2$^b$ | 3840 ± 397.0$^{cd}$ |
| Flow 4 | 1.44 ± 0.070$^a$ | |
| test 4 | 3483 ± 265.1$^b$ | 5006 ± 312.5$^{cd}$ |
| Flow 5 | 2.31 ± 0.197$^a$ | |
| test 5 | 2075 ± 280.2 | 6053 ± 698.0$^{cd}$ |

$^a$t-test for interdependent data: p < 0.05 for Flow 1 Vs Flow "n"
$^b$t-test for interdependent data: p < 0.05 test 3 Vs test 4
$^c$t-test for interdependent data: p < 0.05 comparison of TC 1 Vs TC "n"
$^d$ANOVA orthogonal contrasts: p < 0.05 the sequence TC5 > TC4 > TC3

It was found that at medium flows of from 1.10 ml/min to 1.44 ml/min (Flow 3, Flow 4), the amount of total antioxidant capacity increased. This further confirmed the fact that moderate flows were optimal for standardizing salivary antioxidant power evaluation.

In the context of the current example, the evaluations of salivary flow and relative total antioxidant capacity were determined twice more, namely after 3 and 5 days (Flow 6 and Flow 7 respectively).

The results, shown in Table 9, demonstrated that there were no notable significant variations (ANOVA $p>0.05$) between the values acquired for the stimulated flows on days 1, 3 and 5, thus confirming the high reproducibility of the method of the invention.

TABLE 9

Values for stimulated saliva between 1 ml/min and 1.5 ml/min on subsequent days. Mean values ± SD.

| Days | Variables | Values | Total capacity (TC) [product of Flow × TAS] |
|---|---|---|---|
| 1 | Flow 3 | 1.10 ± 0.082 | |
| | test 3 | 3492 ± 282.2 | 3840 ± 397.0 |
| 3 | Flow 6 | 1.13 ± 0.082 | |
| | test 6 | 3461 ± 254.6 | 3916 ± 452.5 |
| 5 | Flow 7 | 1.14 ± 0.084 | |
| | test 3 | 3493 ± 263.2 | 3983 ± 417.9 |

Example 4

Comparison Between the Method of the Invention and the BAP Test on Saliva and Plasma In this example a comparison was carried out between the method of the invention and the BAP test, which, as related above, was devised and used solely for evaluating the antioxidant power of plasma or serum.

The two methods were compared on the same samples originating from the same subjects and collected at the same times, so as to make the comparison itself as consistent and significant as possible.

12 subjects were selected (6 males and 6 females), ten of whom were the same as those of the previous example. In one of the examined cases, sufficient saliva and blood was withdrawn to be able to determine the coefficient of variation (% CV) after 10 successive determinations.

The current comparison took place in time periods subsequent to those of the previous example.

The admission criteria were identical to those of the previous example. The general characteristics of the subjects are shown below:

| Variable | Values |
|---|---|
| Gender | 6 M and 6 F |
| Age (years) | 29 ± 6.2 |
| Weight (Kg) | 68 ± 10.8 |
| Height (m) | 1.69 ± 0.090 |
| BMI (kg/$m^2$) | 23.6 ± 1.50 |

For the saliva collection, the method given in Example 2 was followed.

The two tests, namely BAP and the method of the invention, were determined on the same sample sequentially. Again using the same sample, the phosphate amount was also determined, by applying the method of Dick and Tabatabai [19] with total sample volume reduced to 1 ml [20]. For said determinations, it was sometimes necessary (when the amount was little more than 1 ml) to repeat saliva collection over two stimulatory sessions (separated by at least 10 minutes). When this happened (only on 2 occasions) the two saliva collections were mixed. The blood for evaluation of phosphates was collected from the brachial vein, an maount of 5 ml being withdrawn into tubes which were centrifuged immediately for separation of the serum. The determinations on both saliva and serum, by using BAP and the method of the invention, were carried out during the morning of the collection. As the determinations by BAP and the method of the invention were carried out on the same samples, the direct comparison had maximum significance, which was independent of all other variables.

All data were processed to calculate the mean and SD values; to evaluate the differences between the two types of test, Student's t-test was applied. Among the various values, the correlation coefficients were also calculated.

Results

All the subjects completed the study, the values for BAP and the method of the invention being shown in Table 10 together with the phosphate contents of blood and saliva.

It should be noted that, while both methods measured the capacity of a fluid to reduce $Fe^{3+}$ and both in terms of μmol/ml of vitamin C, through the BAP test much higher values were obtained than the method of the invention (on average by 57% in saliva and by 30% in serum).

It could be seen that in all cases the BAP determination had to be carried out by reducing the sample volume from 10 μl to 5 μl since with 10 μl, values >3000 μmol/ml were obtained which were at the upper limit of the stated linearity of said BAP test.

TABLE 10

Determinations of antioxidant power of saliva and serum in healthy subjects by BAP test and the method of the invention, compared with the respective initial phosphate levels in saliva and serum (mean values ± SD)

| | Saliva | Serum | Correlations | "r" | P |
|---|---|---|---|---|---|
| Method of the invention (μmol/l) | 3442 ± 387.0 | 1559 ± 176.2 | Saliva Vs Serum | 0.011 | Ns |
| BAP (μmol/l) | 5412 ± 465.6 | 2070 ± 257.1 | Saliva Vs Serum | 0.340 | Ns |
| Phosphates (mg/dl) | 10.5 ± 4.35 | 3.5 ± 0.66 | Salivary phosphates Vs Serum phosphates | 0.875 | <0.05 |
| | | | Serum phosphates Vs BAP serum | 0.635 | <0.05 |
| | | | Salivary phosphates Vs BAP saliva | 0.756 | <0.05 |
| | | | Serum phosphates Vs Method of invention serum | 0.038 | Ns |
| | | | Salivary phosphates Vs Method of invention saliva | −0.085 | Ns |

The % CV measurement in the ten successive determinations were respectively 3.3% for saliva and 2.9% for serum [mean values±SD of the 10 determinations were 3794±126.7 for saliva and 1513±44.0 for serum].

With regard to the correlations, these indicated the existence of a relationship between serum phosphates and salivary phosphates. The most important value for the purposes of the study was the experimental evidence of a direct and significant interference between BAP and phosphates in the determinations in both serum and saliva.

This interference was conveniently not observed for the method of the invention, the results of which were surprising and advantageous independent of the presence of phosphates, thus providing extremely reliable antioxidant power values because of the appropriate selection of components used in said method.

This fact was extremely important for diagnostic purposes, particularly when the biological fluid to be analyzed was saliva, wherein the balance between remineralization and demineralization of enamel can generate phosphate levels even greater than 50 mg/dl, compared to which the BAP has proved to be totally unreliable in determining the real antioxidant power of saliva, actually overestimating the results by 57%.

With regard to serum, the average amounts of phosphates did not exceed 4.5 mg/dl under normal conditions. Nevertheless, the values for total antioxidant power determined by BAP were found to be overestimated even by 33%.

It is apparent from the above that the selection of the inorganic zirconium salts for the reagent of the invention is surprising and advantageous.

Example 5

Comparison Between the Method of the Invention and the BAP Test on Urine

Similarly to Example 4, in this example a comparison was undertaken between the results obtainable with the BAP test and the results obtainable with the method of the invention on urine.

With this aim the same subjects were employed as in Example 4.

Urine was collected at 13.30 hours; the subject was required to empty the bladder at 7.30 in the morning. Afterwards, all urine subsequent to that of 7.30 hours had to be collected in a suitable container and kept in the refrigerator. At 12.30 hours, the subject emptied the bladder into the collection container. In this manner, the amount of urine produced in a 6 hour period was obtained.

Determinations of the antioxidant power of urine according to the two tests were carried out by diluting the urine samples in a 1:5 ratio (1+4) and using relative volumes of 10 μl.

The evaluation of the phosphates in urine was achieved by applying the same method as used for plasma and saliva [19]. In one case, 10 successive evaluations were conducted on the urine sample in order to determine the % CV of the antioxidant power of urine according to the method of the invention.

The mean values and dispersion parameters were calculated on all the data and also the correlations between the urinary phosphate concentrations deriving from the two tests were determined.

Results

All the subjects successfully finished the study in the same analytical laboratory.

The analyses on the urine samples by means of the two tests were conducted on samples diluted 1:5, using 10 μl for the analyses. That same afternoon the phosphate analyses were also carried out.

The results are given in Table 11.

TABLE 11

Determination of the antioxidant power of urine in healthy subjects by BAP and the method of the invention, in relation to the respective initial phosphate levels (mean values ± SD)

| | Urine | Correlations | "r" | P |
|---|---|---|---|---|
| Volume (ml) | 415 ± 82.2 | | | |
| Phosphates (mg/dl) | 281 ± 82.2 | | | |
| Method of the invention (μmol/l) | 1970 ± 265.2 | Method of the invention Vs. Phosphates | 0.095 | Ns |
| BAP (μmol/l) | 4210 ± 590.4 | BAP Vs. Phosphates | 0.706 | <0.05 |

By studying the data, it followed that the values according to the method of the invention clearly differed from those of BAP and that the average values of BAP actually exceeded those of the method of the invention by 110%, due to the high phosphate content in urine. Indeed, again in this case a significant interference by phosphates on the BAP test was confirmed, as was deduced from the correlation between the BAP test values and phosphates ($r=0.706$, $p<0.05$).

However, as far as the method of the invention is concerned, it was surprisingly and advantageously confirmed that there was no correlation between the values found for antioxidant power and amount of phosphates present in the samples.

The % CV of the method of the invention for urine proved to be 3.7% [derived from the mean value±SD equal to 1820±66.7].

Example 6

Evaluation of the Antioxidant Power of Saliva According to the Method of the Invention, Before and After Its Centrifugation For this example, 20 subjects were evaluated (10 males and 10 females) frequenting a dental clinic for their routine check-up.

Subjects with prostheses were also included, but patients affected by periodontal disease or with dental abscesses were excluded.

The only requirement was to previously clean the teeth with toothpaste and/or dental floss after eating breakfast or lunch or any food item or beverage prior to the observation period.

The tests were performed over the course of the same day between 10.00 and 19.00 hours.

The general characteristics of the examined subjects are given below:

| Variable | Values |
|---|---|
| Gender | 10 M and 10 F |
| Age (years) | 40 ± 15.0 |
| Weight (Kg) | 70 ± 8.1 |
| Height (m) | 1.68 ± 0.091 |
| BMI (kg/m$^2$) | 24.9 ± 2.61 |

Saliva collection followed the methodology illustrated in the preceding Example 2.

The t-test for interdependent data was applied to the values obtained before and after centrifugation in order to determine whether the differences were statistically significant. The determination was performed on 5 μl of saliva and the value was multiplied by 2.

The results are shown in Table 12.

TABLE 12

Determinations of the antioxidant power of saliva according to the method of the invention, before and after centrifugation (mean values ± SD)

| | Values |
|---|---|
| Volume of saliva (ml) | 1.1 ± 0.20 |
| Det. before centrifugation (μmol/l) | 2760 ± 354.0 |
| Det. after centrifugation (μmol/l) | 2741 ± 360.7 |

$p > 0.05$ t-test for interdependent data

As it follows from the mean data and statistical analysis, there were no significant differences between the values obtained before and after centrifugation, as the components used in the method of the invention, particularly the zirconium salts, surprisingly and advantageously did not induce precipitation of the phosphates, but effectively masked their presence while maintaining them in solution.

Example 7

Evaluation of TAS in a Comparison Between Normal Subjects and Those Affected by Paradontosis In the current example, the levels of salivary antioxidant power were evaluated by comparing apparently healthy subjects with those affected by paradontosis of differing clinical degrees. 100 subjects were placed under observation, subdivided into two groups of 50 subjects each.

All the subjects frequented the same dental surgery for their dental hygiene.

It was hence possible to identify those subjects who simply undertook six monthly or annual dental check-ups as well as subjects undergoing treatment for paradontopathies of varying degrees.

The levels of paradontosis were distinguished using a 1 to 4 semi-quantal scale whereby 1 represents the "mild" level and 4 the "severe" level. Severity was determined mainly from the number of dental arch quadrants affected by the disease, as well as the degree of gum damage (retraction of the gums and inflammation of the gums).

Subjects affected by paradontosis also had other associated pathologies, mainly hypertension and/or dislipidemia; patients were only admitted if they were under therapeutic control with treatment having been established for at least two months.

Admission criteria for the apparently healthy subjects did not permit any other pathology or current pharmacological or supplementary treatments.

All the subjects were fasted from the evening prior to the examination. The subjects were tested for salivary antioxidant power at least one hour after the normal autonomous hygiene procedures (brushing teeth with toothpaste) and before being subjected to any other dental check. Saliva was collected at a temperature of 25° C. from comfortably seated subjects according to the methodology indicated in Example 2.

If the volume was not of the required amount of 1 to 1.5 ml, the saliva collection was repeated after a rest of at least 10 minutes.

The mean values and dispersion parameters were calculated on the data; also, to clearly show the differences between the groups, Student's t-test was applied. In addition, the correlation coefficient was determined between the results of the method of the invention and the severity of paradontosis.

The general characteristics of the subjects are shown below:

| Variables | Healthy subjects | Subjects with paradontosis | t-test |
|---|---|---|---|
| Gender | 25 M; 25 F | 23 M; 27 F | |
| Age | 39 ± 9.5 | 32 ± 8.3 | $p < 0.05$ |
| Concomitant pathology | | | |
| Hypertension and/or dislipidemia | 0 | 16 | |
| Arthrosis | 0 | 6 | |
| Type II diabetes | 0 | 8 | |

Those subjects affected by paradontosis were noted as being significantly younger than the healthy subjects.

Evaluations of the salivary antioxidant power values, the relative salivary flow and the degree of paradontosis are given in Table 13.

TABLE 13

Comparison between healthy subjects and subjects affected by paradontosis. Mean values ± SD.

| Variables | Healthy subjects | Subjects with paradontosis | t-test |
|---|---|---|---|
| Paradontosis index | 0 | 2.1 ± 0.92 | |
| Volume (ml/min) | 1.21 ± 0.17 | 1.17 ± 0.15 | Ns |
| Method of the invention (μmol/l) | 2032 ± 332.1 | 1212 ± 220.6 | $p < 0.05$ |

It was found that, although salivary flows did not actually differ significantly between subjects affected by paradontosis, the salivary flow test often had to be repeated for these latter due to scanty production.

In view of the significant difference in ages between the two groups, the statistical analysis was corrected for age, but the differences in salivary flow values were found nevertheless to be significant, as they indicated that in subjects affected by paradontosis the antioxidant power of saliva was reduced.

Moreover, an inversely proportional correlation was noted between the severity of paradontosis and the antioxidant power values of the relative saliva ("r"–0.544 p<0.05). This confirmed the experimental evidence, as shown and commentated on above with reference to Table 3.

Example 8

Evaluation of the Antioxidant Power of Certain Foods and Beverages According to the Method of the Invention The method of the invention was used to determine the antioxidant power of a series of foods and beverages which can contain different amounts of phosphates.

For each product, 5 batches of different origin were examined and the evaluations were conducted for all samples on the same day of collection and then simultaneously on subsequent days.

The results are given in Table 14.

TABLE 14

Determinations of the antioxidant power of beverages and foods

| Product | Method of the invention (μmol/l) | Average portion (ml or g) | Total portion (Vitamin C μmol equiv.) |
|---|---|---|---|
| Lemons[a] | 11373 ± 140.5 | 20 | 1137 ± 14.0 |
| Oranges[b] | 2460 ± 273.4 | 120 | 1476 ± 164.1 |
| Tomatoes[c] | 1113 ± 11.9 | 150 | 835 ± 8.9 |
| Blueberries[d] | 1318 ± 66.1 | 40 | 264 ± 13.2 |
| Raspberries[e] | 4556 ± 100.0 | 40 | 911 ± 20.0 |
| Chianti wine[f] | 5426 ± 81.9 | 120 | 651 ± 81.9 |
| Soave wine[g] | 4711 ± 93.4 | 120 | 565 ± 11.2 |
| Rose` wine[h] | 5645 ± 200.5 | 120 | 677 ± 24.1 |
| Port wine[i] | 4536 ± 56.0 | 40 | 181 ± 2.2 |
| Beer[l] | 1408 ± 47.3 | 330 | 465 ± 15.6 |
| Grappa[m] | 162 ± 18.5 | 40 | 6 ± 0.7 |
| Brandy[n] | 312 ± 38.1 | 40 | 12 ± 1.5 |
| Coffee[o] | 7945 ± 185.9 | 30 | 1192 ± 27.9 |
| Tea[p] | 3840 ± 114.1 | 150 | 576 ± 17.1 |

[a]Verdello lemons [Type: Scelgobio ® - origin Italy Cat. II Size code 4/5]
[b]Blood oranges [Type: Mariarosa - origin Italy Cat. I Size code 6]
[c]Tomatoes for pulping [origin Italy]
[d]Blueberries [Type: Vitalberry - origin Chile Cat. I]
[e]Raspberries [Type: Natberry Maroc - origin Morocco Cat. I]
[f]Chianti Classico [Producer: Cecchi - origin Italy]
[g]Soave Cadis [Producer: Cantina di Soave - origin Italy]
[h]Rose` Salento [Producer: Al Tralcio Antico - origin Italy]
[i]Tawny Port [Producer: Offley - origin Portugal]
[l]Dreher [Producer: Dreher - origin italy]
[m]Pinot Nero Grappa [Producer: La Versa - origin Italy]
[n]Fundador [Producer: Pedro Domecq - origin Spain]
[o]Nespresso [Type: Roma - origin Italy]
[p]Twinings ® [Type: Earl Grey - origin UK]

The coffee, prepared using a Nespresso automatic machine, was of Caffè Roma type quality. 5 different coffees were prepared in an amount of 30 ml.

With regard to tea, Twinings® tea bags were used [Classic Earl Grey]; samples were prepared by infusing one tea bag for 3 minutes in 150 ml of water which was used 2 minutes after it had boiled.

The fruit and tomatoes, representative of any fruit and vegetables, were homogenized and diluted with deionized water in a 1:5 ratio. All the samples were then centrifuged at 800 rpm for 2 minutes and the determination was carried out on 10 μl of supernatant.

Should the determination have exceeded 6000 μmol/l (e.g. for coffee and lemon), the measurement was repeated using 5 μl and the value was multiplied by 2.

Table 14 also shows the values of total antioxidant power of food portions. It surprisingly follows from these data that the antioxidant values of a white wine (Soave) and a rosè wine (Salento) are not significantly different from those of the red wine (Chianti). Among the foods analyzed, oranges, coffee and lemons are those with the highest antioxidant power.

From the detailed description and the aforegiven examples, the advantages achieved by means of the reagent and the method of the present invention are evident. In particular, said reagent enables the presence of phosphates in samples of biological and vegetal fluids to be masked, thus advantageously avoiding said phosphates interfering with the antioxidant power determination while at the same time maintaining them in solution, i.e. avoiding their precipitation which would disadvantageously incur a dedicated separation step. Said advantages are particularly appreciated in terms of the practicality and cost effectiveness of implementing the method. Said method of the invention, also by virtue of the kit comprising said reagent, enables the antioxidant power in biological and vegetal fluids to be evaluated in a reliable, reproducible, repeatable and economically convenient manner, thus overcoming the aforenoted disadvantages of the known methods, and in particular the disadvantages noted in relation to the BAP test.

BIBLIOGRAPHICAL REFERENCES

1) Percival R S, Challacombe S J, Marsh P D. Flow rates of resting whole and stimulated parotid saliva in relation to age and gender. J Dent Res. 1994; 73:1416-1420.
2) Del Vigna de Almeda P, Trindade Grècio A, Naval Machado A et al. Saliva composition and functions: a comprehensive review. J Cont Dent Pract. 2008; 9:1-11.
3) Humphrey S P, Williamson R T. A review of saliva: normal composition, flow, and function. J Prost Den 2001; 85:162-169.
4) Battino M, Ferreiro M S, Gallardo I et al. The antioxidant capacity of saliva. J Clin Periodontol 2002; 29:189-194.
5) Moore S, K A C Calder, Miller N J, C A Rice-Evans. Antioxidant activity of saliva and periodontal disease. Free Rad Res 1994; 21:417-425.
6) Meyle J, Kapitza K. Assay of ascorbic acid in human crevicular fluid from clinically healthy gingival sites by high-performance liquid chromatography. Arch Oral Biol 1990; 35:319-323.
7) Nagler R M, Klein I, Zarhevsky N et al. Characterization of the differentiated antioxidant profile in human saliva. Free Rad Biol Med 2002; 32:268-277.
8) Iwamoto Y, Nakamura R, Watanabe T, Tsunemitsu A. Heterogenity of peroxidase related to antibacterial activity in human parotid saliva. J Dent Res 1972; 51:503-508.
9) Thomas E L, Milligan T W, Joyner R E, Jefferson M M. Antibacterial activity of hydrogen peroxide and the lactoperoxidase-hydrogen peroxide-thiocyanate system against oral streptococci. Infect Immun 1994; 62:529-535.
10) Grisham M B, Ryan E M. Cytotoxic properties of salivary gland. Am J Physiol 1990; 258:C115-C121.
11) Kou F, Takahama U. Hydrogen peroxide-induced luminescence and evolution of molecular oxygen saliva. Arch Oral Biol 1995; 40:15-21.
12) Borges I, Machado-Moreira E A, Filho D W et al. Proinflammatory and oxidative stress markers in patients with periodontal disease. Med Inflamm 2007; ID 45794: 1-5
13) Huang D, Ou B, Prior R L. The chemistry behind antioxidant capacity assays. Agr Food Chem 2005; 53:1841-1856.
14) Magalhães L M, Segundo M A, Reis S, Lima J L F C. Methodological aspects about in vitro evaluation of antioxidant properties. Anal Acta 2008; 613:1-19.
15) Hirayama O, Tagaki M, Hukumoto K, Katoh S. Evaluation of antioxidant activity by chemiluminescence. Anal Biochem 1997; 247:237-241.
16) Hirayama O, Yida M. Evaluation of hydroxyl radical-scavenging ability by chemiluminescence. Anal Biochem 1997; 251:297-299.
17) Kohen R, Beit-Yannai E, Berry E M, Tirosh O. Overall low molecular weight antioxidant activity of biological fluids and tissues by cyclic voltammetry. Method Enzymol 1999; 300:285-296.
18) Celi P, Sullivan M, Evans D. The stability of the reactive oxygen metabolites (d-ROMs) and biological antioxidant potential (BAP) tests on stored horse blood, Vet J 2010; 183:217-218.
19) Dick W A, Tabatabai M A. Determination of Orthophosphates in aqueous solutions containing labile organic and inorganic phosphorus compounds. J Environ Qual 1977; 6:82-85.
20) He Z, Griffin T, Honeycutt C W. Phosphorus distribution in dairy manures. J Environ Qual 2004; 33:1528-1534.
21) Benzie I F F, Strain J J. The ferric reducing ability of plasma (FRAP) as a measure of "antioxidant power": The FRAP assay. Anal Biochem 1996; 239:70-76.
22) Composizione degli alimenti-Aggiornamento 2000 Istituto Nazionale di Ricerca per gli Alimenti e la Nutrizione Ed EDRA Medical Publishing & New Media.

What is claimed is:

1. Method for determining the antioxidant power of a biological fluid or a vegetal fluid comprising the steps of:

a) providing an alcoholic thiocyanate solution;

b) adding at least one reagent comprising an inorganic zirconium salt and at least one solvent to the alcoholic thiocyanate solution, said at least one solvent being a water-lower alcohol mixture, to generate a first intermediate mixture;

c) adding an aqueous ferric salt solution comprising a ferric salt to the first intermediate mixture to form a second intermediate mixture;

d) measuring an absorbance of the second intermediate mixture to obtain a first absorbance value;

e) adding a sample of the biological fluid or the vegetal fluid to the second intermediate mixture to generate a sample-containing solution;

f) measuring an absorbance of the sample-containing solution to obtain a second absorbance value;

g) subtracting the first absorbance value from the second absorbance value to generate a corrected absorbance value; and h) comparing the corrected absorbance value to a standard calibration curve obtained by performing steps a) through g) on a plurality of samples comprising vitamin C and obtaining a value for antioxidant power of the biological fluid or the vegetal fluid as vitamin C equivalents, according to Lambert-Beer's law.

2. The method of claim 1, wherein said ferric salt is selected from the group consisting of a fluoride salt, a chloride salt, a bromide salt, an iodide salt, a carbonate salt, a sulphate salt, and a nitrate salt.

3. The method of claim 2, wherein said ferric salt is a nitrate salt.

4. The method of claim 1, wherein the inorganic zirconium salt of the first intermediate mixture and said ferric salt are in a molar ratio of 20:1 to 5:1.

5. The method of claim 1, wherein said sample of the biological fluid or the vegetal fluid has a first volume and the second intermediate mixture has a second volume, and wherein the first volume and the second volume are in a volumetric ratio of 1:250 to 1:50.

6. The method of claim 1, wherein said biological fluid is selected from the group consisting of saliva, serum, plasma, urine, tears, and sweat, and wherein the vegetal fluid is a fluid obtained from the group consisting of fruit, vegetables, food, wine, beer, beverages, coffee and tea.

7. The method of claim 1, wherein said inorganic zirconium salt of the reagent of step b) is selected from the group consisting of a fluoride salt, a chloride salt, a bromide salt, an iodide salt, a carbonate salt, a sulphate salt, a nitrate salt, and mixtures thereof.

8. The method of claim 7, wherein said inorganic zirconium salt is selected from the group consisting of a fluoride salt, a chloride salt, a bromide salt, an iodide salt, and mixtures thereof.

9. The method of claim 8, wherein said inorganic zirconium salt is $ZrCl_4$.

10. The method of claim 1, wherein said lower alcohol of the reagent of step b) is a linear or branched alcohol.

11. A kit for implementing the method of claim 1, comprising:

i) at least one reagent comprising an inorganic zirconium salt and at least one solvent, said at least one solvent being a water-lower alcohol mixture;

ii) at least one alcoholic thiocyanate solution;

iii) at least one aqueous ferric salt solution; and iv) an illustrated leaflet comprising instructions for carrying out a determination of a value of antioxidant power according to steps a)-h) of the method of claim 1.

12. The kit of claim 11, wherein said i) at least one reagent and said ii) at least one alcoholic thiocyanate solution are one single solution.

13. The kit of claim 11, wherein said illustrated leaflet further comprises instructions for collecting a biological fluid sample or a vegetal fluid sample.

14. The kit of claim 13, further instructions for collection of a sample of the biological fluid when said biological fluid is saliva, wherein the further instructions state that said sample is collected under conditions of salivary flow of 0.70 to 1.50 ml/min.

15. The kit of claim 11, wherein said inorganic zirconium salt of the at least one reagent of i) is selected from the group consisting of a fluoride salt, a chloride salt, a bromide salt, an iodide salt, a carbonate salt, a sulphate salt, a nitrate salt, and mixtures thereof.

16. The kit of claim 15, wherein said inorganic zirconium salt is selected from the group consisting of a fluoride salt, a chloride salt, a bromide salt, an iodide salt, and mixtures thereof.

17. The kit of claim 16, wherein said inorganic zirconium salt is $ZrCl_4$.

18. The kit of claim 11, wherein said lower alcohol of the reagent of i) is a linear or branched alcohol.

* * * * *